US011132750B2

(12) United States Patent
Malone (10) Patent No.: US 11,132,750 B2
(45) Date of Patent: Sep. 28, 2021

(54) SYSTEMS AND METHODS FOR UTILIZING AN OBJECTIVE IMPAIRMENT INJURY SCORE RISK MODEL

(71) Applicant: MedPros, LLC, Warner Robins, GA (US)

(72) Inventor: K. Scott Malone, Warner Robins, GA (US)

(*) Notice: Subject to any disclaimer, the term of this patent is extended or adjusted under 35 U.S.C. 154(b) by 127 days.

(21) Appl. No.: 16/448,769

(22) Filed: Jun. 21, 2019

(65) Prior Publication Data

US 2020/0402176 A1   Dec. 24, 2020

(51) Int. Cl.
*G06Q 40/08* (2012.01)
*G16H 50/30* (2018.01)

(52) U.S. Cl.
CPC ............ *G06Q 40/08* (2013.01); *G16H 50/30* (2018.01)

(58) Field of Classification Search
CPC .............................. G06Q 40/08; G06Q 40/00
USPC ......................................................... 705/35
See application file for complete search history.

(56) References Cited

U.S. PATENT DOCUMENTS

2016/0034662 A1\* 2/2016 Moynihan ............... G16H 50/30
705/2
2018/0117446 A1\* 5/2018 Tran ..................... G06Q 20/389

\* cited by examiner

*Primary Examiner* — Kirsten S Apple
(74) *Attorney, Agent, or Firm* — FisherBroyles, LLP (57) ABSTRACT

Various embodiments are directed to utilizing an objective impairment injury score risk model. A computing device may receive injury data from a user. The computing device may then perform a security action that protects against unauthorized sharing of the injury data by storing the injury data as a group of linked blocks in a distributed computing system. The computing device may then utilize a machine-learning model to generate a set of questions for the user. The questions may be utilized to determine weighting factors associated with the injury data. The computing device may then utilize the machine-learning model to determine an impairment injury score based on the weighting factors. The may include an objectively determined value associated with a degree of impairment resulting from an injury described in the injury data. Finally, the computing device may display an injury risk management report, based on the score, to the user.

10 Claims, 4 Drawing Sheets

SYSTEMS AND METHODS FOR UTILIZING AN OBJECTIVE IMPAIRMENT INJURY SCORE RISK MODEL

BACKGROUND

Risk managers (e.g., in the healthcare industry, insurance industry and employers) are often required to obtain a determination of the degree of impairment and associated disability from injuries incurred during an individual's employment and/or in the performance of their professional duties. The injuries may be on a scale of a non-reportable minor medical injury to a complete catastrophic injury leaving an individual unemployable for suitable and sustainable occupational work thus totally disabled.

The concept of determining a medical and physical impairment is as much an art as a science. Physicians are often required to review medical records, ask injured parties (e.g., athletes) about current problems, examine their bodies, and review diagnostic studies. Predicting who will stay healthy and who will get hurt is an art. It is even more difficult to determine permanent functional impairments as a result of injuries. Conventional systems for assessing injuries in athletes are based on systems such as the American Medical Association (AMA) guidelines. However, the AMA guides only provide a framework for impairments. The AMA guides assumes every profession is the same (i.e., apples to apples). Thus, AMA impairment ratings do not adequately take into account the impact of an individual's impairment on his or her job performance. In particular, the impairment incurred as a result of injury may lead to a detrimental effect on an individual's career. For example, a professional athlete or entertainer incurring an injury during a game or a performance may file an insurance claim to recover compensation in the form of current and future expenses (e.g., medical bills and costs), losses in the form of lost income or lost wages, pain and suffering damages, and/or emotional distress damages, based on an assessment of impairment and or disability associated with the injury. Furthermore, traditional methods for assessing impairment often include the use of subjective approaches (e.g., computations and algorithms) configured to assist in the calculation of insurance claim settlements. As mentioned above, one of the primary problems with these approaches is that they are not designed to take into account various injury related variables such as the occupation of an injured party, employment duties, and/or the loss of supplemental income. It is with respect to these considerations and others that the various embodiments of the present invention have been made.

SUMMARY

As will be described in greater detail below, the instant disclosure describes various systems and methods for utilizing an objective injury impairment score risk model.

In one example, a method for utilizing an objective injury impairment score risk model may include (1) receiving, by a computing device, injury data from a user, (2) performing, by the computing device, a security action that protects against unauthorized sharing of the injury data by storing the injury data as a plurality of linked blocks in a distributed computing system, (3) generating, by the computing device and utilizing a machine-learning model, one or more questions for the user, where the questions are utilized for receiving user answers to determine a plurality of weighting factors associated with the injury data, (4) determining, by the computing device and utilizing the machine-learning model, an impairment injury score based on the injury data and the weighting factors, where the impairment injury score includes an objectively determined value associated with a degree of impairment resulting from an injury described in the injury data, and (5) displaying, by the computing device, an injury risk management report based on the impairment injury score to the user.

In some examples, the injury data may include one or more medical records associated with the injury from a medical provider. Additionally or alternatively, the injury data may include one or more medical records associated with the injury from an insurance provider. Additionally or alternatively, the injury data may include one or more medical records associated with the injury from a legal services provider.

In some examples, the security action may include storing the injury data as a blockchain comprising the plurality of linked blocks in the distributed computing system. In one example, a smart contract may be utilized between the user and a provider of the injury data for communicating the injury data on the blockchain.

In some examples, the questions may include a query for an occupation for an injured party associated with the injury data, employment duties of an injured party associated with the injury data, and/or income sources of an injured party associated with the injury data. In some examples, the injury data may be determined by (1) accessing, in real-time, a group of injury data sources to retrieve objective data associated with the injury data and the weighting factors and (2) computing the impairment injury score based on the objective data.

In some examples, the weighting factors may include occupation data, employment duty data, and/or income source data. In some examples, the injury data sources may include a disability data source, an occupational and environmental medicine data source, an insurance data source, a managed care data source, a work loss data source, and/or a labor and statistics data source.

In one example, a system for utilizing an objective impairment injury score model may include at least one processor and a memory storing computer-executable instructions that when executed by the at least one processor, cause the system to (1) receive, by a computing device, injury data from a user, (2) perform, by the computing device, a security action that protects against unauthorized sharing of the injury data by storing the injury data as a plurality of linked blocks in a distributed computing system, (3) generate, by the computing device and utilizing a machine-learning model, one or more questions for the user, where the questions are utilized for receiving user answers to determine a group of weighting factors associated with the injury data, (4) determine, by the computing device and utilizing the machine-learning model, an impairment injury score based on the injury data and the weighting factors, where the impairment injury score includes an objectively determined value associated with a degree of impairment resulting from an injury described in the injury data, and (5) display, by the computing device, an injury risk management report based on the impairment injury score to the user.

In some examples, the security action may include storing the injury data as a blockchain comprising the plurality of linked blocks in the distributed computing system. In one example, a smart contract may be utilized between the user and a provider of the injury data for communicating the injury data on the blockchain.

In some examples, the questions may include a query for an occupation for an injured party associated with the injury data, employment duties of an injured party associated with the injury data, and/or income sources of an injured party associated with the injury data. In some examples, the injury data may be determined by (1) accessing, in real-time, a group of injury data sources to retrieve objective data associated with the injury data and the weighting factors and (2) computing the impairment injury score based on the objective data.

In some examples, the weighting factors may include occupation data, employment duty data, and/or income source data. In some examples, the injury data sources may include a disability data source, an occupational and environmental medicine data source, an insurance data source, a managed care data source, a work loss data source, and/or a labor and statistics data source.

In some examples, the above-described method may be encoded as computer-readable instructions on a non-transitory computer-readable medium. For example, a non-computer-readable medium may include one or more computer-executable instructions that, when executed by at least one processor of a computing device, may cause the computing device to (1) receive, by the computing device, injury data from a user, (2) perform, by the computing device, a security action that protects against unauthorized sharing of the injury data by storing the injury data as a plurality of linked blocks in a distributed computing system, (3) generate, by the computing device and utilizing a machine-learning model, one or more questions for the user, where the questions are utilized for receiving user answers to determine a group of weighting factors associated with the injury data, (4) determine, by the computing device and utilizing the machine-learning model, an impairment injury score based on the injury data and the weighting factors, where the impairment injury score includes an objectively determined value associated with a degree of impairment resulting from an injury described in the injury data, and (5) display, by the computing device, an injury risk management report based on the impairment injury score to the user.

In some examples, the security action may include storing the injury data as a blockchain comprising the plurality of linked blocks in the distributed computing system. In one example, a smart contract may be utilized between the user and a provider of the injury data for communicating the injury data on the blockchain.

In some examples, the questions may include a query for an occupation for an injured party associated with the injury data, employment duties of an injured party associated with the injury data, and/or income sources of an injured party associated with the injury data. In some examples, the injury data may be determined by (1) accessing, in real-time, a group of injury data sources to retrieve objective data associated with the injury data and the weighting factors and (2) computing the impairment injury score based on the objective data.

In some examples, the weighting factors may include occupation data, employment duty data, and/or income source data. In some examples, the injury data sources may include a disability data source, an occupational and environmental medicine data source, an insurance data source, a managed care data source, a work loss data source, and/or a labor and statistics data source.

BRIEF DESCRIPTION OF THE FIGURES

The accompanying drawings illustrate a number of example embodiments and are a part of the specification. Together with the following description, these drawings demonstrate and explain various principles of the instant disclosure.

DETAILED DESCRIPTION OF EXAMPLE EMBODIMENTS

Various embodiments of the disclosure are directed to systems and methods for utilizing an objective impairment injury score risk model. As will be described in greater detail below, the systems and methods described herein may enable a user to utilize a machine-learning model for generating a set of questions, based on received injury data in a computing system, for determining a group of weighting factors. The weighting factors may be utilized by the machine-learning model, in conjunction with dynamically updated historical data from injury and occupation data sources, user feedback, and/or user analysis, to generate an objective injury rating (e.g., an impairment injury score) for determining a degree of impairment sustained as a result of an injury. The machine-learning model may utilize a combination of predictive modeling techniques coupled with adaptive risk factor analysis. In this way, the systems and methods described herein may provide an objective rating system that allows risk managers to provide insurance companies and other interested parties with an injury scoring model to determine the degree of impairment sustained as a result of injury.

The embodiments of the disclosure described herein provide several advantages over traditional methods utilizing subjective techniques for determining impairment injury scores and resulting degrees of impairment. Advantages include the utilization of machine-learning to incorporate data from non-injury sources, such as occupation, occupation requirements, and income data sources, to provide impairment injury scores indicative of an objective (e.g., fair) assessment of injury impairments than would otherwise be provided. For example, injury impairment scores determined traditional techniques may underweight the impact of injuries for injured parties involved in high-risk occupations such as professional athletics, construction, entertainment, certain medical professions (e.g. surgeons), heavy machine operators, public service (e.g., police/fire), etc., thereby resulting in reduced insurance payments for disabilities associated with these types of injuries. Additional advantages include providing objective data for compliance with current and future liability insurance standards (e.g., Federal Accounting Standard Board (FASB) requirements).

In addition, the systems and methods described herein may improve the security of a computing device by protecting against the unauthorized sharing of the injury data through the use of blockchain technology. For example, the systems and methods herein may store the injury data as a plurality of linked blocks in a distributed computing system thereby preventing access to this sensitive data by malicious actors. In addition, the systems and methods described herein provide a machine-learning model capable of receiving, analyzing, and performing computations on large data sets on a computing device, functionality that may not be performed solely by a human being.

Embodiments of the disclosure now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

System Overview

Figure 1:
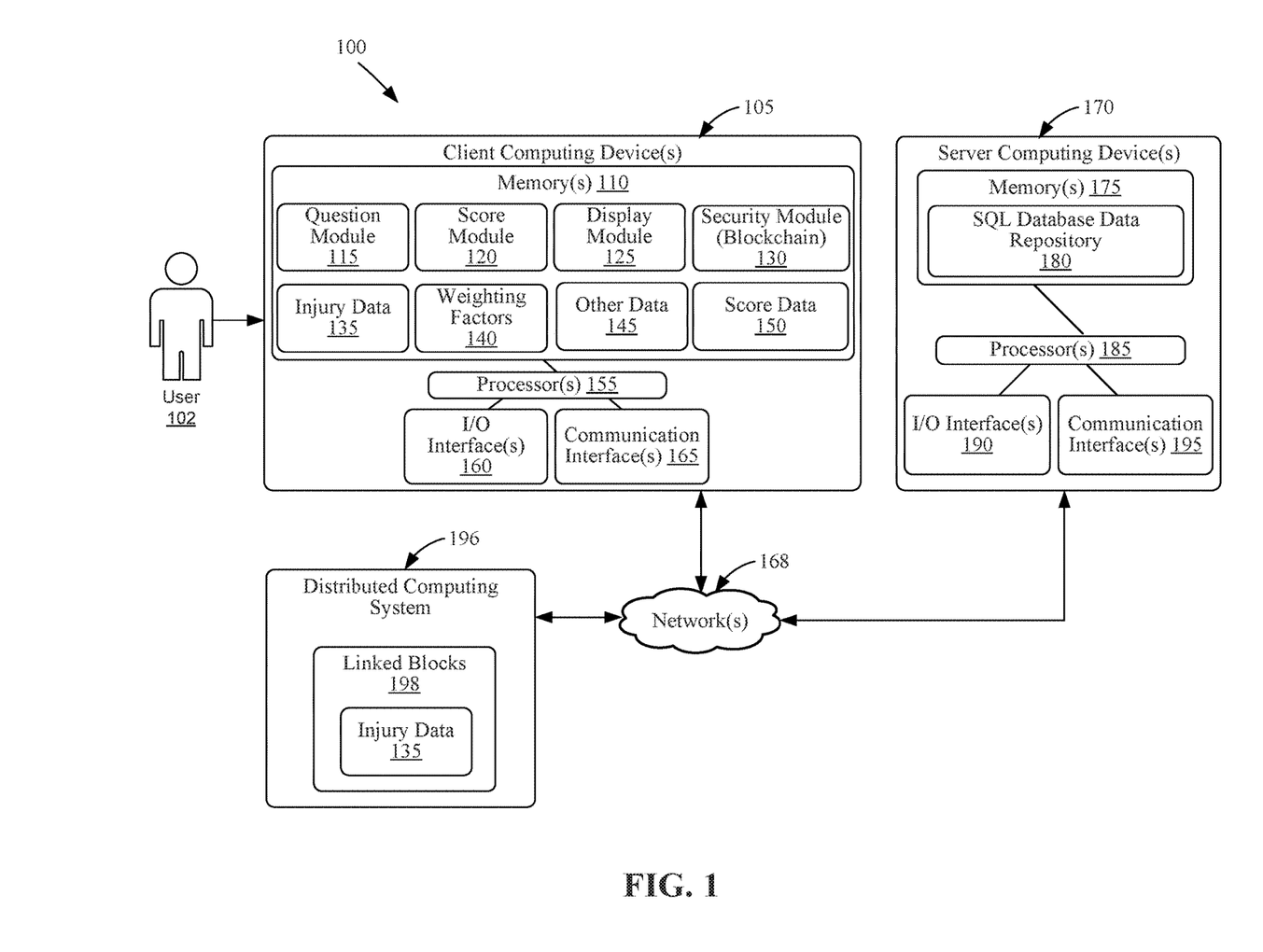
FIG. 1 illustrates a block diagram of an example system for utilizing an objective impairment injury score risk model, according to an example embodiment.

FIG. 1 illustrates a block diagram of a system 100 for utilizing an objective impairment injury score risk model, according to an example embodiment. With reference to FIG. 1, system 100 may include a user 102, one or more client computing devices 105, one or more server computing devices 170, and a distributed computing system 196 (which may optionally include one or more client computing devices 105 and/or one or more server computing devices 170) in communication over network 168.

Client computing device 105 generally represents any type or form of computing device capable of reading computer-executable instructions. In some examples, client computing device 105 may include, but is not limited to, a mobile device (e.g., a mobile phone, Personal Digital Assistants (PDAs), smartphone, tablet computing device, etc.), a desktop computing device, a laptop computing device, servers, multimedia players, embedded systems, wearable devices (e.g., smart watches, smart glasses, etc.), gaming consoles, combinations of one or more of the same, or any other suitable computing device. Client computing device 105 may utilize one or more processors 155 to execute computer-readable instructions that facilitate the general operation of client computing device 105 and facilitating utilizing an objective impairment injury score risk model.

In addition to having one or more processors 155, client computing device 105 may further include and/or be associated with one or more memory devices 110 (hereinafter "memory 110"), input/output ("I/O") interface(s) 160, and/or communication and/or network interface(s) 165. Memory 110 may be any non-transitory computer-readable medium, coupled to processor(s) 155, such as random access memory ("RAM"), read-only memory ("ROM"), and/or a removable storage device. Memory 110 may store a wide variety of data files and/or various program modules, such as a question module 115, score module 120, a display module 125, a security (e.g., blockchain) module 130, injury data 135, weighting factors 140, other data 145, data 150, and an operating system ("OS") (not shown). The aforementioned data files and/or program modules may include any suitable data or instructions that facilitates the operation of client computing device 105 and/or interaction of client computing device 105 with one or more other components of the system 100. For example, question module 115 may be a component of a machine-learning model that includes instructions for generating one or questions for user 102 to determine weighting factors 140 associated with injury data 135. Additionally, score module 120 may be a component of a machine-learning model that determines an impairment injury score (e.g., score data 150) based on injury data 135 and weighting factors 140. Additionally, display module 125 may be a component of a machine-learning model configured to display an injury risk management report based on an impairment injury score (e.g., score data 150) to user 102. In some examples, the injury risk management report may also be included in score data 150. Additionally, security module 130 may be a component of a machine-learning model (or optionally a separate component on client computing device 105) configured perform a security action that protects against the unauthorized sharing of injury data 135 by storing injury data 135 as a group of linked blocks 198 in distributed computing system 196.

The OS may be any suitable module that facilitates the general operation of the client computing device 105 as well as the execution of other program modules. For example, the OS may be, but is not limited to, a suitable mobile OS or a specially designed operating system. As desired, client computing device 105 may additionally include one or more communication modules that facilitate interaction with other computing devices and/or other communications functionality. For example, a suitable near field communication module, radio frequency module, Bluetooth module, or other suitable communication module may be included in client computing device 105.

With continued reference to client computing device 105, the one or more I/O interfaces 160 may facilitate communication between client computing device 105 and one or more input/output devices; for example, one or more user interface devices, such as a display, a keypad, a mouse, a pointing device, a control panel, a touch screen display, a remote control, a microphone, a speaker, etc., that facilitate user interaction with client computing device 105. The one or more network and/or communication interfaces 165 may facilitate connection of client computing device 105 to one or more suitable networks and/or communication links. In this regard, client computing device 105 may receive and/or communicate information to other components of the system 100, such as server computing device 170, and/or other devices and/or systems.

Server computing device 170 generally represents any type or form of computing device capable of reading computer-executable instructions. For example, as desired, server computing device 170 may include any number of processor-driven devices or systems, including but not limited to, cloud-based or dedicated application servers, a mobile computer, an application-specific circuit, a minicomputer, a microcontroller and/or any other processor-driven devices or systems configured to run certain software applications for receiving and processing large amounts of data. In some embodiments, server computing device 170 may utilize one or more processors 185 to execute computer-readable instructions that facilitate the general operation of server computing device 170 and that manage data in an SQL database data repository 180.

In addition to having one or more processors 185, server computing device 170 may further include and/or be associated with one or more memory devices 175 (hereinafter "memory 175"), input/output ("I/O") interface(s) 190, and/or communication and/or network interface(s) 195. The memory 175 may be any non-transitory computer-readable medium, coupled to processor(s) 185, such as random access memory ("RAM"), read-only memory ("ROM"), and/or a removable storage device. Memory 175 may store a wide variety of data files and/or various program modules, such as SQL database data repository 180 and an operating system ("OS") (not shown). The aforementioned data files may include any suitable data that facilitates the operation of server computing device 170 and/or interaction of server computing device 170 with one or more other components of system 100. For example, data files may include SQL database data repository 180 that may be utilized for storing data accessed from various injury data sources utilized by a machine-learning model to determine an impairment injury score associated with a degree of impairment resulting from an injury described in injury data 135.

The OS may be suitable module that facilitates the general operation of server computing device 170, as well as the execution of other program modules. For example, the OS may be, but is not limited to, Microsoft Windows®, Apple OSX™, UNIX, LINUX, a mainframe computer operating system (e.g., IBM z/OS, MVS, OS/390, etc.), or a specially designed operating system.

Distributed computing system 196 may include any distributed configuration of client/and or server computing devices utilized for securely storing data (e.g., injury data 135) received from client computing device 105 and/or server computing device 170. In some examples, distributed computing system 196 may include a centralized distributed computing network including client computing device 105 (serving as a central node), server computing device 170, and one or more other computing devices (not shown) utilized for implementing blockchain security methods for data storage and/or retrieval. In other examples, distributed computing system 196 may include a decentralized distributed computing network including client computing device 105, server computing device 170, and one or more other computing devices (not shown) utilized for implementing blockchain security methods for data storage and/or retrieval.

Network(s) 168 may include any telecommunication or computer network (e.g., an intranet, a wide area network, a local area network, a personal area network, the Internet, a cellular or mobile network, etc.) that may be utilized to facilitate communication between client computing device 105, server computing device 170, and distributed computing system 196.

I/O interface 190 may facilitate communication between server computing device 170 and one or more input/output devices; for example, one or more user interface devices, such as a display, a keypad, a touch screen display, a microphone, a speaker, etc., that facilitate user interaction with server computing device 170. Network and/or communication interfaces 195 may facilitate connection of server computing device 170 to one or more suitable networks, for example, network 168. In this regard, server computing device 170 may receive and/or communicate information to other components of system 100 (such as client computing device 105 and/or distributed computing system 196).

System 100 as shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. Accordingly, embodiments of the disclosure should not be construed as being limited to any particular operating environment, system architecture, or device configuration.

Figure 2:
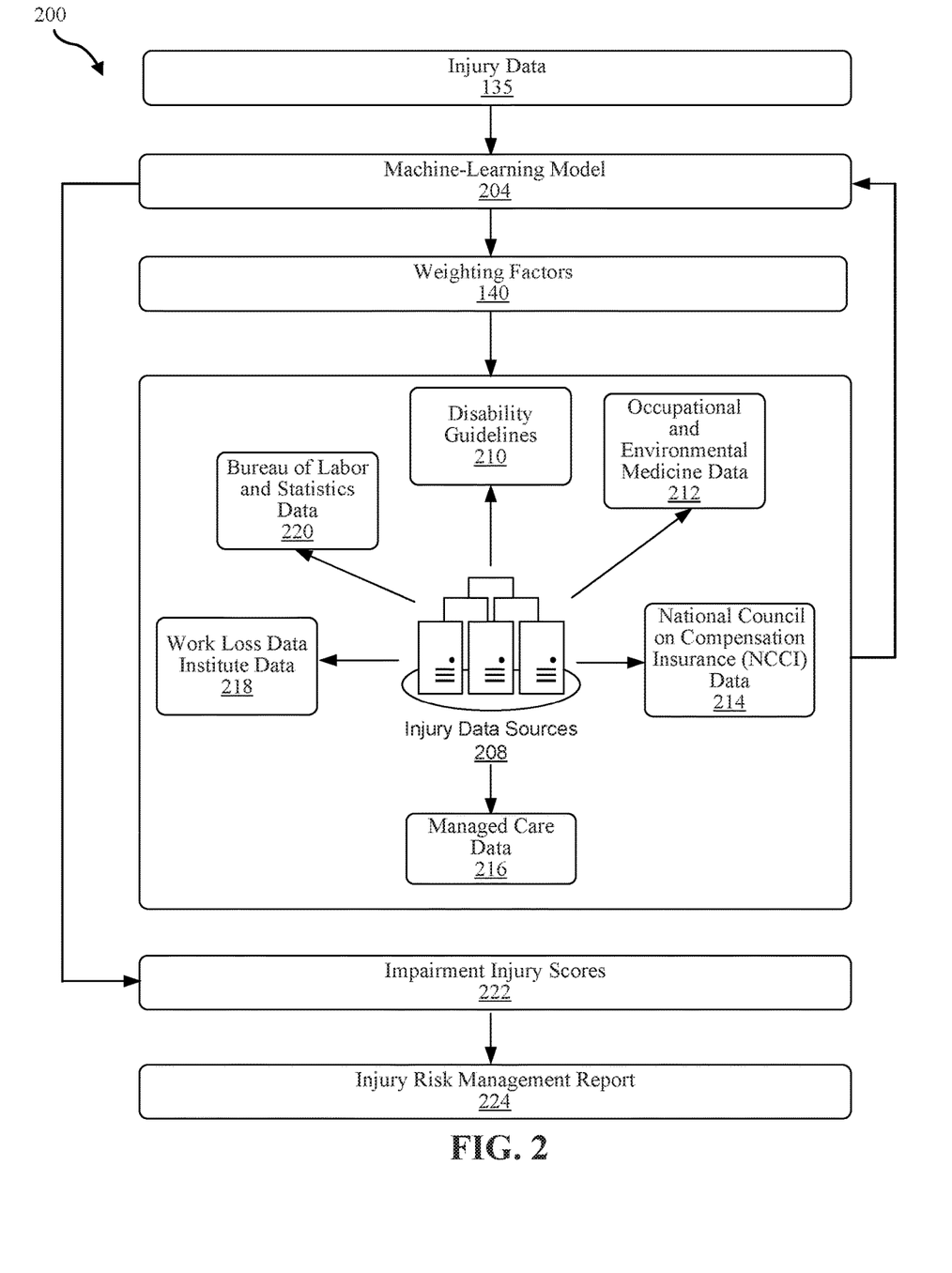
FIG. 2 illustrates a block diagram of an additional example system for utilizing an objective impairment injury score risk model, according to an example embodiment.

FIG. 2 illustrates a block diagram of an example system 200 for utilizing an objecting impairment injury score risk model. The system 200 may include a machine-learning model 204. As will be described in greater detail below with respect to FIG. 3, machine-learning model 204 may receive injury data 135 describing one or more injuries from a user. Machine-learning model 204 may then apply weighting factors 140 (determined based the user's responses to generated questions based on injury data 135) to injury data 135. Next, machine-learning model 204 may access injury data sources 208 to retrieve data utilized in determining impairment injury scores 222. In some examples, injury data sources 208 may include, without limitation, disability guidelines 210 (e.g., the American Medical Association (AMA) guide to impairment and disability guidelines), occupational and environmental medicine data 212 (e.g., American College of Occupational and Environmental Medicine data), National Council on Compensation Insurance (NCCI) data 214, managed care data 216, Work Loss Data Institute data 218, and Bureau of Labor and Statistics data 220. In some embodiments, impairment injury scores 208 may include objectively determined values associated with a degree of impairment resulting from an injury described in injury data 135. Finally, based on impairment injury scores 222, an impairment injury score risk management report 224 may be generated and displayed (utilizing machine-learning model 204) to a user.

Operational Overview

Figure 3:
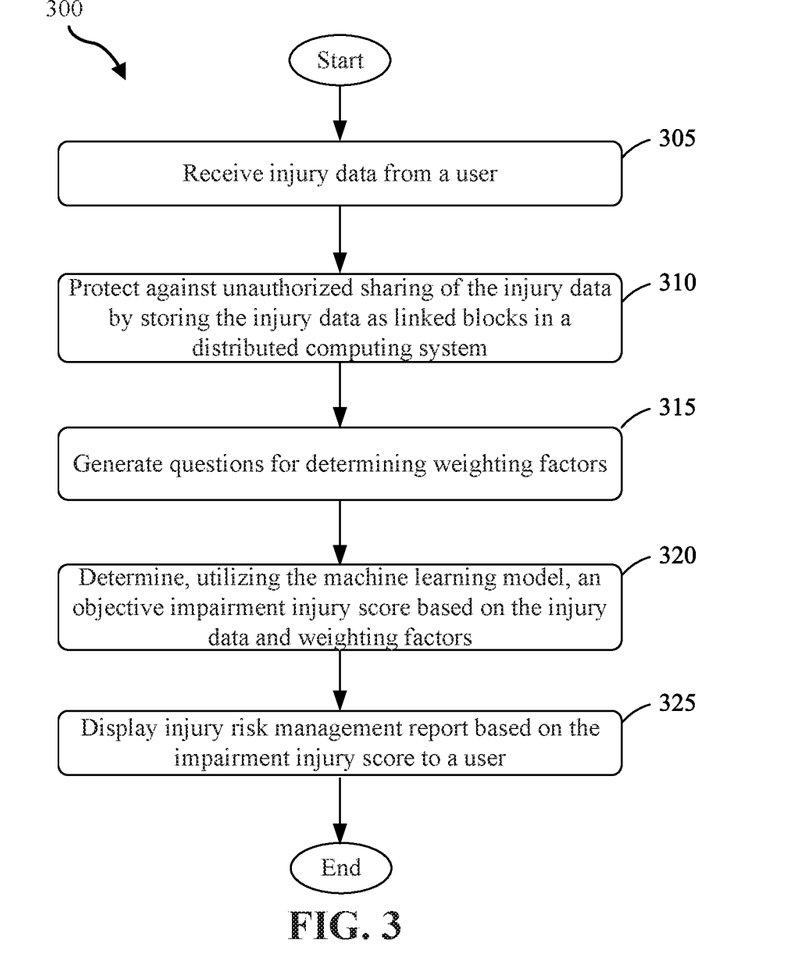
FIG. 3 illustrates a flow diagram of an example process for utilizing an objective impairment injury score risk model, according to an example embodiment.

FIG. 3 illustrates a flow diagram of an example process 300 for utilizing an objective impairment injury score risk model, according to an example embodiment. The steps shown in FIG. 3 may be performed by any suitable computer-executable code and/or computing system, including system 100 in FIG. 1, system 200 in FIG. 2, and/or variations or combinations of one or more of the same. In one example, each of the steps shown in FIG. 3 may represent an algorithm whose structure includes and/or is represented by multiple sub-steps, examples of which will be provided in greater detail below.

As illustrated in FIG. 3, at step 305 one or more of the systems described herein may receive injury data from a user. For example, security module 130 may, as part of client computing device 105 in FIG. 1, receive injury data 135 from user 102 for encryption (e.g., via blockchain) and communicating to question module 115.

The term "injury data," as used herein, generally refers to any data describing injuries or disabilities associated with one or more injured parties. In some examples, injury data may include medical records maintained by a responsible party such as a medical provider, an insurance provider, and/or a legal services provider.

Security module 120 may receive injury data 135 in a variety of ways. In some examples, security module 120 may receive injury data 135 as one or more medical records associated with an injury from a medical provider. Additionally or alternatively, security module 120 may receive injury data 135 as one or more medical records associated with the injury from an insurance provider (e.g., for processing a claim). Additionally or alternatively, security module 120 may receive injury data 135 as one or more medical records associated with the injury from legal services provider (e.g., for review by an expert witness in a litigation matter).

At step 310, one or more of the systems described herein may protect against unauthorized sharing of the injury data by storing the injury data as linked blocks in a distributed computing system. For example, security module 120 may, as part of client computing device 105 in FIG. 1, protect against unauthorized sharing of injury data 135 by storing injury data 135 as linked blocks 198 in distributed computing system 196.

Security module 120 may store injury data 135 in a variety of ways. In some examples, security module 120 may store injury data 135 as a blockchain. In some examples, security module 130 the blockchain may include a smart contract between user 102 and a provider of injury data 135. In some embodiments, security module 120 may be configured to (1) receive a request for an impairment injury score rating (e.g., security module 120 may receive a request for an injury impairment injury score 222 from user 102) and (2) broadcast the request over a network (e.g., security module 120 may broadcast the request to distributed computing system 196 over network 168). Upon receiving the request, a network (e.g., distributed computing system 196) may validate the request using cryptography (i.e., blockchain encryption methods) to ensure privacy. A transaction (including the request, injury data 135 and weighting factors 140) may then be represented as one or more blockchain blocks to be stored and subsequently sent as data for independent medical examination (IME) and functional tests. Data generated by the IME and functional tests may then be sent to a data repository (e.g., SQL database data repository 180) for analysis by a machine-learning model utilizing explainable AI, analytics and prognostic report data which may be added as additional blocks to the existing blockchain. The request may then be completed with findings allowing an impairment injury score (e.g., an impairment injury score 222) to be used to value an injury based on an injured party's occupation (e.g., profession).

The term "blockchain," as used herein, generally refers to any decentralized and distributed or centralized and distributed network of computing devices in which information is secured through the construction of linked blocks representing the information. Each block may be utilized to store information up to a data capacity associated with the block, after which the block is added a link in the blockchain after receiving approval from every other device linked to the chain (e.g., protocol). In some examples, the protocol process includes requiring the generation of a cryptographic hash before a new block may be added to the chain. The security of the information stored in the blockchain is increased with each addition of a new block as the blockchain is copied onto every computing device associated with a single block. As a result, the computing power required to "break" the blockchain (i.e., gain unauthorized access to the stored information) increases exponentially with each new block. In some examples, a blockchain may be implemented according to a variety of models. These models may include, without limitation, Blockchain as a service (BaaS), development platforms, blockchain based software, network fee charge, blockchain professional services, and/or peer-to-peer (P2P) block chain business models. In some examples, a blockchain may be a permissive or private blockchain in which access to data (e.g., medical records) is restricted to only authorized individuals or entities having a provided unique address and password. In some examples, a private blockchain may be centralized and distributed blockchain providing customizability and control over the network to the individual or organization deploying as they may decide who participates in the network. As a result, fewer resources may be invested in competing to secure the network as compared to decentralized blockchains. Moreover, private blockchains may have a higher overall throughput as the hardware that the network runs on may be decided upon by the participants. In practice, this means that individuals or entities may use private blockchains to store sensitive information among trusted nodes without having to make the sensitive information public.

The term "smart contract," as used herein, generally refers to an automated contract between two parties on a blockchain with terms agreed upon by both parties. Once the terms of the contract are carried out, an algorithm may be utilized to deliver information and document the transaction on the blockchain. Smart contracts thus may eliminate the need for centralized authorities to verify the transactions including the delivery of information.

At step 315, one or more of the systems described herein may generate questions for determining weighting factors based on the injury data received at step 305. For example, machine-learning model 204 may, as part of client computing device 105 in FIG. 1, be utilized to generate one or more questions for user 102. Machine-learning model 204 may utilize the questions for receiving user answers to determine weighting factors 140 associated injury data 135. In one example, machine-learning model 204 may include question module 115 that may be configured to generate questions for determining weighting factors 140 based on injury data 135.

The term "machine-learning model," as used herein, generally refers to utilizing statistical techniques to provide computer systems the ability to "learn" (e.g., progressively improve performance on a specific task) from data, without being explicitly programmed. In some examples, machine learning models may utilize ensemble learning methods for classification, regression, and other tasks for generating one or more predictive outputs (e.g., outputs based on predictive modeling) based on provided input data. In some examples, machine-learning models may include artificial intelligence (AI), neural networks, cognitive modeling, and/or predictive modeling. In some embodiments, AI may include, without limitation, machine learning AI and explainable AI. Machine learning AI may include big data sets (e.g., data that is received in large amounts) that may be fed into an algorithm so that the algorithm train itself and learn. Explainable AI may include machine-learning techniques that make it possible for human users to understand, appropriately trust, and effectively manage AI. Explainable AI may include human led, machine supported methods including (i) a human that analyzes and produces insights using a portfolio of tools, (ii) the human makes decisions based on optimized machine prescriptions, and (iii) the human acts or executes the decisions. Additionally or alternatively, explainable AI may include machine led, human supported methods including (i) a machine analyzes and produces insights with human review, (ii) a human makes decisions based on optimized machine prescriptions, and (iii) the human acts or executes the decisions with machine oversight. Example machine learning models may include, without limitation, support vector machine models, logistic regression models, random forest models, and deep neural network (DNN) models.

Machine-learning model 204 may generate questions based on injury data 135 in a variety of ways. In some embodiments, machine-learning model 204 may generate queries for an occupation for an injured party associated with injury data 135, employment duties of an injured party associated with injury data 135, and/or income sources of an injured party associated with injury data 135. For example, if injury data 135 includes data relating to an anterior cruciate ligament (ACL) injury associated with an injured party, machine-learning model 204 may, based on rules defined by user 102, query user 102 whether the injured party has an occupation requiring a high level of physical activity (e.g., professional or amateur athletics, construction, public service, etc.), the employment duties of the inured party (e.g., running back, soccer (football) player, dancer, construction worker, fireman, policeman, etc.), and/or income sources such as contract values, endorsements (e.g., supplemental income), etc. Based on user-supplied answers to the aforementioned questions, machine-learning model 204 may determine weighting factors 140. Additionally or alternatively, user 102 may submit weighting factors 140 directly to machine-learning model 204 in response to query generated by machine-learning model 204.

Figure 4:
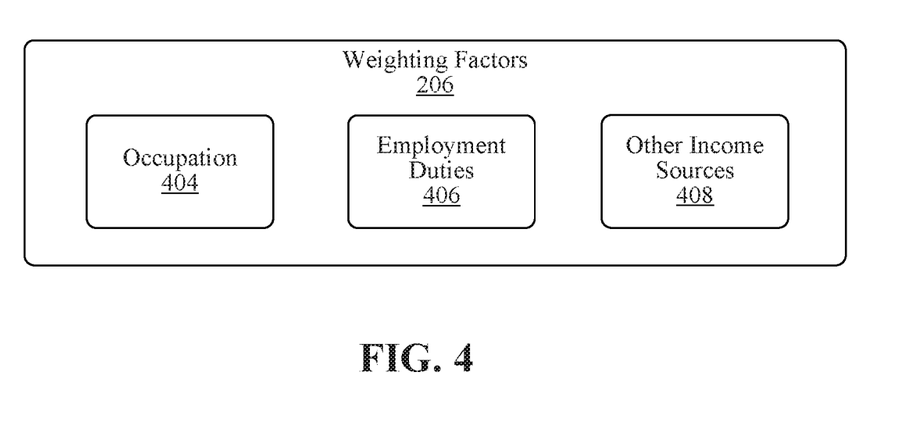
FIG. 4 illustrates a block diagram showing example weighting factors that may be utilized in the example systems for utilizing an objective impairment injury score risk model of FIGS. 1 and 2, according to an example embodiment.

Turning now to FIG. 4 example weighting factors 140 are shown in accordance with various embodiments described herein. In some embodiments, weighting factors 140 may include occupation 404, employment duties 406, and/or other income sources 408. Returning now to step 315 of FIG. 3, machine-learning model 204 may utilize one or more weighting factors 140 in determining which injury data sources 208 to access in order to determine impairment injury scores 222.

At step 320, one or more of the systems described herein may determine, utilizing the machine-learning model, an impairment injury score based on the injury data and the weighting factors. For example, machine-learning model 204 may, as part of client computing device 105 in FIG. 1, be utilized to determine an impairment injury score 222 based on injury data 135 and weighting factors 140. In one example, machine-learning model 204 may include score module 120 that may be configured to determine an impairment injury score 222 based on injury data 135 and weighting factors 140. In some examples, an impairment injury score 222 may be a numerical value determined from one or more objective injury data sources (e.g., injury sources 208) that is associated with a degree of impairment resulting from an injury described in injury data 135. For example, an impairment injury score 222 for a professional athlete incurring a knee injury will have a higher numerical value (and thus representing a higher degree of impairment) as compared to an office worker with a desk job incurring the same injury due to the athlete's occupation and occupational duties requiring a higher level of knee function (e.g., for running, jumping, etc.) than the office worker's occupation and occupational duties. In addition, the athlete's potential income received for performing his/her primary occupation (as well as secondary income received from other sources (e.g., endorsement income)) may also be more adversely affected as compared to other occupations, thereby resulting in a higher impairment injury score 222. As another example, an impairment injury score 222 for a professional vocalist incurring a vocal cord injury will have a higher numerical value (and thus representing a higher degree of impairment) as compared to an instrumentalist incurring the same injury due to the vocalist's occupational duties requiring a higher level of larynx (i.e., voice box) function than the instrumentalist's occupational duties. In addition, the vocalist's potential income received for performing his/her primary occupational duties (as well as secondary income received from other sources (e.g., endorsement income) for performing the same duties) may also be more adversely affected, thereby resulting in a higher impairment injury score 222. As yet another example, an impairment injury score 222 for a surgeon incurring a musculoskeletal or nerve injury in their dominant hand will have a higher numerical value (and thus representing a higher degree of impairment) as compared to a medical practitioner who does not perform surgery (e.g., a family medicine or internal medicine physician) incurring the same injury due to the surgeon's occupational duties requiring a higher level of motor control and coordination. As yet another example, an impairment injury score 222 for a concert pianist or a concert violinist incurring a hand injury will also have a higher numerical value (and thus representing a higher degree of impairment) as compared to a vocalist in a musical group or band (who does not play an instrument) incurring the same injury due to their occupational duties requiring the use of one or both of their hands.

Machine-learning model 204 may be utilized to determine impairment injury scores 222 in a variety of ways. In some embodiments, machine-learning model 204 may be utilized to (i) access, in real-time, injury data sources 208 to retrieve objective data associated with injury data 135 and weighting factors 140 and (ii) compute an impairment injury score 222 based on the objective data. For example, machine-learning model 204 may be utilized to retrieve objective data including one or more of disability guidelines 210 (e.g., American Medical Association (AMA) disability guidelines), occupational and environmental medicine data 212 (e.g., American College of Occupational and Environmental Medicine data), National Council on Compensation Insurance (NCCI) data 214, managed care data 216, Work Loss Data Institute data 218, and/or Bureau of Labor and Statistics data 220, from injury data sources 208. In some embodiments, the aforementioned objective data may be stored in SQL database data repository 180 on server computing device 170. In some examples, machine-learning model 204 may be configured to detect when each of injury data sources 208 has been updated and subsequently request the most recent data such that any current and/or new data (e.g., data updates) are received in real-time. Upon receiving the objective data from injury data sources 208, machine-learning model 204 may then apply weighting factors 140 to determine an impairment injury score 222. For example, occupation, employment duties, and income source weighting factors may be applied to information retrieved from disability guidelines 210, occupational and environmental medicine data 212, and work loss data institute data 218 regarding the effects of knee injuries on professional athletes with respect to the ability to return and/or the average length of their respective careers post-injury as well as loss of income due to being injured. In some examples, user 102 may review and evaluate the data retrieved from injury data sources 208 by machine-learning model 204 for accuracy and provide feedback thereon. For example, user 102 may be a physician who, based on his/her knowledge and experience, may determine if one or more of injury data sources 208 selected by machine-learning model 204 (or alternatively, any of the data retrieved from injury data sources 208) is applicable to injury data 135 and provide helpful feedback (e.g., discarding/failing inaccurate data or approving accurate data). Thus, in this way, user 102 may effectively "train" machine-learning model 204 to more accurately generate impairment injury scores 222. For example, based on the feedback received, machine-learning model 204 may be updated to generate different questions intended to elicit responses that will improve the selection of injury data sources 208 associated with injury data 135 and weighting factors 140.

At step 325, one or more of the systems described herein may display an injury risk management report based on the impairment injury score determined at step 320 to a user. For example, machine-learning model 204 may, as part of client computing device 105 in FIG. 1, be utilized to generate and display injury risk management report 224 to user 102.

Machine-learning model 204 may be utilized to generate and display injury risk management report 224 to user 102 in a in a variety of ways. In some embodiments, machine-learning model 204 generate a report including an impairment injury score 222 for an injured party associated with injury data 135 and weighting factors 140 for display on client computing device 105. In one example, injury risk management report 224 may describe a degree of impairment associated with an injury for an insurance claim. Additionally or alternatively, injury risk management report 224 may describe a degree of impairment associated with an injury for a litigation claim associated with an injury. For example, injury risk management report 224 may be utilized in support of satisfying evidentiary rules regarding the admissibility of expert witness testimony related to the effect an injury may have on an injured party's ability to continue to perform the duties of their chosen occupation, future income, etc.

The example process 300 may end following step 325.

Various embodiments of the invention are described above with reference to block and flow diagrams of systems, methods, apparatuses, and/or computer program products according to example embodiments. It will be understood that one or more blocks of the block diagrams and flow diagrams, and combinations of blocks in the block diagrams and the flow diagrams, respectively, can be implemented by computer-executable program instructions. Likewise, some blocks of the block diagrams and flow diagrams may not necessarily need to be performed in the order presented, or may not necessarily need to be performed at all, according to some embodiments.

Various block and/or flow diagrams of systems, methods, apparatus, and/or computer program products according to example embodiments are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments.

The computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. The computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks.

As an example, embodiments may provide for a computer program product, comprising a computer-readable medium having a computer-readable program code or program instructions embodied therein, said computer-readable program code adapted to be executed to implement one or more functions specified in the flow diagram block or blocks. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special purpose, hardware-based computer systems that perform the specified functions, elements or steps, or combinations of special purpose hardware and computer instructions.

The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

In addition, one or more of the modules described herein may transform data, physical devices, and/or representations of physical devices from one form to another. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A computer-implemented method for utilizing an objective impairment injury score risk model, at least a portion of the method being performed a computing device comprising at least one processor, the method comprising:
   receiving, by the computing device, injury data from a user;
   performing, by the computing device, a security action that protects against unauthorized sharing of the injury data, by one or more malicious actors, by storing the injury data as a plurality of linked blocks as a permissive blockchain comprising a smart contract between the user and a provider of the injury data in a distributed computing system, wherein the injury data is stored by:
      receiving a request for an impairment injury score from the user; and
      broadcasting the request to the distributed computing system, wherein upon receiving the request, the distributed computing system validates the request by utilizing a blockchain encryption method comprising cryptography to encrypt the injury data, thereby improving a security of the computing device by restricting access to the injury data;

generating, by the computing device and utilizing a machine-learning model, a plurality of questions for the user, wherein the questions are utilized for receiving user answers to determine a plurality of weighting factors associated with the injury data, wherein the questions comprise a query for an occupation for an injured party associated with the injury data, a query for employment duties of an injured party associated with the injury data, and a query for income sources of an injured party associated with the injury data, and wherein the weighting factors comprise each of the following: occupation data, employment duty data, and income source data;

determining, by the computing device and utilizing the machine-learning model, an impairment injury score based on the request, the injury data, and the weighting factors, wherein the request, the injury data, and the weighting factors are represented as a plurality of blockchain blocks in the permissive blockchain for sending to a data repository for storage, wherein determining the impairment injury score comprises:

accessing, in real-time, a plurality of injury data sources to retrieve objective data associated with the injury data and the weighting factors; and computing the impairment injury score based on the objective data, wherein the impairment injury score comprises an objectively determined value associated with a degree of impairment resulting from an injury described in the injury data; and displaying, by the computing device, an injury risk management report based on the impairment injury score to the user; and training, by the computing device, the machine-learning model utilizing user feedback to the generated questions, wherein, based on the user feedback, the machine-learning model generates different questions to elicit responses that increases an accuracy of the determined impairment injury score based on a change in a selection of the injury data sources comprising the objective data associated with the injury data and the weighting factors.

2. The computer-implemented method of claim 1, wherein receiving the injury data comprises receiving one or more medical records associated with the injury from a medical provider.

3. The computer-implemented method of claim 1, wherein receiving the injury data comprises receiving one or more medical records associated with the injury from an insurance provider.

4. The computer-implemented method of claim 1, wherein receiving the injury data comprises receiving one or more medical records associated with the injury from a legal services provider.

5. The computer-implemented method of claim 1, wherein the injury data sources comprise:
a disability data source;
an occupational and environmental medicine data source;
an insurance data source;
a managed care data source;
a work loss data source; and
a labor and statistics data source.

6. A system for utilizing an objective impairment injury score risk model, the system comprising:
at least one processor; and
at least one memory storing computer-executable instructions that when executed by the at least one processor, cause the system to:

receive, by a computing device, injury data from a user;

perform, by the computing device, a security action that protects against unauthorized sharing of the injury data, by one or more malicious actors, by storing the injury data as a plurality of linked blocks as a permissive blockchain comprising a smart contract between the user and a provider of the injury data in a distributed computing system, wherein the injury data is stored by:

receiving a request for an impairment injury score from the user; and broadcasting the request to the distributed computing system, wherein upon receiving the request, the distributed computing system validates the request by utilizing a blockchain encryption method comprising cryptography to encrypt the injury data, thereby improving a security of the computing device by restricting access to the injury data;

generate, by the computing device and utilizing a machine-learning model, a plurality of questions for the user, wherein the questions are utilized for receiving user answers to determine a plurality of weighting factors associated with the injury data, wherein the questions comprise a query for an occupation for an injured party associated with the injury data, a query for employment duties of an injured party associated with the injury data, and a query for income sources of an injured party associated with the injury data, and wherein the weighting factors comprise each of the following: occupation data, employment duty data, and income source data;

determine, by the computing device and utilizing the machine-learning model, an impairment injury score based on the request, the injury data, and the weighting factors, wherein the request, the injury data, and the weighting factors are represented as a plurality of blockchain blocks in the permissive blockchain for sending to a data repository for storage, wherein determining the impairment injury score comprises:

accessing, in real-time, a plurality of injury data sources to retrieve objective data associated with the injury data and the weighting factors; and computing the impairment injury score based on the objective data, wherein the impairment injury score comprises an objectively determined value associated with a degree of impairment resulting from an injury described in the injury data;

display, by the computing device, an injury risk management report based on the impairment injury score to the user; and train, by the computing device, the machine-learning model utilizing user feedback to the generated questions, wherein, based on the user feedback, the machine-learning model generates different questions to elicit responses that increases an accuracy of the determined impairment injury score based on a change in a selection of the injury data sources comprising the objective data associated with the injury data and the weighting factors.

7. The system of claim 6, wherein the injury data is received by receiving one or more medical records associated with the injury from a medical provider.

8. The system of claim 6, wherein the injury data is received by receiving one or more medical records associated with the injury from an insurance provider.

9. The system of claim 6, wherein the injury data is received by receiving one or more medical records associated with the injury from a legal services provider.

10. A non-transitory computer-readable medium comprising one or more computer-executable instructions that, when executed by at least one processor of a computing device, cause the computing device to:

receive, by a computing device, injury data from a user;

perform, by the computing device, a security action that protects against unauthorized sharing of the injury data, by one or more malicious actors, by storing the injury data as a plurality of linked blocks as a permissive blockchain comprising a smart contract between the user and a provider of the injury data in a distributed computing system, wherein the injury data is stored by:

receiving a request for an impairment injury score from the user; and         broadcasting the request to the distributed computing system, wherein upon receiving the request, the distributed computing system validates the request by utilizing a blockchain encryption method comprising cryptography to encrypt the injury data, thereby improving a security of the computing device by restricting access to the injury data;

generate, by the computing device and utilizing a machine-learning model, a plurality of questions for the user, wherein the questions are utilized for receiving user answers to determine a plurality of weighting factors associated with the injury data, wherein the questions comprise a query for an occupation for an injured party associated with the injury data, a query for employment duties of an injured party associated with the injury data, and a query for income sources of an injured party associated with the injury data, and wherein the weighting factors comprise each of the following: occupation data, employment duty data, and income source data;

determine, by the computing device and utilizing the machine-learning model, an impairment injury score based on the request, the injury data, and the weighting factors, wherein the request, the injury data, and the weighting factors are represented as a plurality of blockchain blocks in the permissive blockchain for sending to a data repository for storage, wherein determining the impairment injury score comprises:

accessing, in real-time, a plurality of injury data sources to retrieve objective data associated with the injury data and the weighting factors; and         computing the impairment injury score based on the objective data, wherein the impairment injury score comprises an objectively determined value associated with a degree of impairment resulting from an injury described in the injury data;

display, by the computing device, an injury risk management report based on the impairment injury score to the user; and     train, by the computing device, the machine-learning model utilizing user feedback to the generated questions, wherein, based on the user feedback, the machine-learning model generates different questions to elicit responses that increases an accuracy of the determined impairment injury score based on a change in a selection of the injury data sources comprising the objective data associated with the injury data and the weighting factors.

\* \* \* \* \*